United States Patent [19]

Rozzell

[11] Patent Number: 5,019,509

[45] Date of Patent: May 28, 1991

[54] METHOD AND COMPOSITIONS FOR THE PRODUCTION OF L-ALANINE AND DERIVATIVES THEREOF

[75] Inventor: J. David Rozzell, Cambridge, Mass.

[73] Assignee: Genetics Institute, Inc., Cambridge, Mass.

[21] Appl. No.: 183,860

[22] Filed: Apr. 20, 1988

[51] Int. Cl.$^5$ .................... C12N 1/21; C12N 15/60; C12N 15/63; C12N 13/06

[52] U.S. Cl. .................... 435/232; 435/71.1; 435/116; 435/170; 435/172.1; 435/172.3; 435/252.3; 435/320.1; 536/27; 935/6; 935/9; 935/22; 935/59; 935/60; 935/61; 935/66; 935/72

[58] Field of Search .................... 435/41, 116, 172.3, 435/176, 253.3, 252.33, 69.1, 71.1, 116, 170, 172.1, 172.3, 320, 6, 9, 22, 59, 60, 61, 66, 72; 536/72

[56] References Cited

U.S. PATENT DOCUMENTS 4,681,852 7/1987 Tribe et al. .................... 435/108

OTHER PUBLICATIONS

Tabor et al., Methods in Enzymology XVIIA pp. 681–692 Kakimoto et al., J. Biol. Chem. 244(2), 353–8.

*Primary Examiner*—Richard A. Schwartz
*Assistant Examiner*—Richard C. Peet
*Attorney, Agent, or Firm*—Luann Cserr; Bruce M. Eisen; David L. Berstein

[57] ABSTRACT

This invention provides genes encoding aspartate beta decarboxylase, vectors containing the genes, microbial host cells transformed with the vectors, and the use of such transformed host cells and compositions derived therefrom to produce L-alanine and certain derivatives thereof.

8 Claims, 4 Drawing Sheets

FIGURE 1A

-102
TG CGTTGGCCAA TGTGTTCCTG ACTTTGTTGG GTCCGCTGGT

-43
CATTGCCTTT GCGTGAAACC CCTGAACTGA TTCACTAGGA CGAATGGAAG GAGTTGCGAT

```
                17
ATG AGC AAG GAT TAT CAG AGT CTG GCG AAC TTG AGC CCG TTT GAG CTC
Met Ser Lys Asp Tyr Gln Ser Leu Ala Asn Leu Ser Pro Phe Glu Leu

77
AAG GAT GAG TTG ATC AAG ATC GCC TCG GGC GAC GGA AAC CGC CTC ATG
Lys Asp Glu Leu Ile Lys Ile Ala Ser Gly Asp Gly Asn Arg Leu Met

137
CTC AAT GCG GGG CGG GGC AAT CCC AAT TTT CTG GCA ACC ACC CCG AGA
Leu Asn Ala Gly Arg Gly Asn Pro Asn Phe Leu Ala Thr Thr Pro Arg

AGA GCA TTT TTC CGT CTG GGC TTG TTC GCG GCT GCC GAG TCG GAA CTT
Arg Ala Phe Phe Arg Leu Gly Leu Phe Ala Ala Ala Glu Ser Glu Leu

197
TCG TAT TCA TAT ATG AAC ACG GTG GGC GTG GGA GGC CTG GCA AAG ATC
Ser Tyr Ser Tyr Met Asn Thr Val Gly Val Gly Gly Leu Ala Lys Ile

257
GAG GGC ATA GAA GGG CGC TTC GAG CGC TAT ATT GCC GAG AAC CGC GAT
Glu Gly Ile Glu Gly Arg Phe Glu Arg Tyr Ile Ala Glu Asn Arg Asp

317
CAG GAA GGC GTG CGC TTT CTC GGT AAA TCC CTG AGT TAT GTA CGC GAT
Gln Glu Gly Val Arg Phe Leu Gly Lys Ser Leu Ser Tyr Val Arg Asp

377
CAG CTG GGC TTG GAT CCG GCC GCC TTC CTG CAC GAG ATG GTC GAC GGT
Gln Leu Gly Leu Asp Pro Ala Ala Phe Leu His Glu Met Val Asp Gly

ATT CTG GGC TGC AAT TAC CCC GTT CCC CCT CGG ATG CTG AAC ATC
Ile Leu Gly Cys Asn Tyr Pro Val Pro Pro Arg Met Leu Asn Ile
```

FIGURE 1B

```
          437
AGC GAA AAA ATC GTG CGC CAG TAC ATC ATC CGT GAA ATG GGG GCC GAT
Ser Glu Lys Ile Val Arg Gln Tyr Ile Ile Arg Glu Met Gly Ala Asp

497
GCA ATT CCC AGC GAG TCC GTG AAC CTG TTT GCG GTC GAG GGG GGA ACG
Ala Ile Pro Ser Glu Ser Val Asn Leu Phe Ala Val Glu Gly Gly Thr

557
GCC GCC ATG GCA TAC ATC TTC GAG AGC ATG AAG GTC AAC GGC CTC CTC
Ala Ala Met Ala Tyr Ile Phe Glu Ser Met Lys Val Asn Gly Leu Leu

617
AAG GCT GGT GAC AAG GTA GCC ATC GGC ATG CCG GTT TTC ACT CCG TAC
Lys Ala Gly Asp Lys Val Ala Ile Gly Met Pro Val Phe Thr Pro Tyr

ATA GAA ATT CCG GAA CTG GCC CAG TAT GCG TTG GAG GAG GTG GCA ATC
Ile Glu Ile Pro Glu Leu Ala Gln Tyr Ala Leu Glu Glu Val Ala Ile

677
AAT GCC GAC CCG GCC CTC AAC TGG CAA TAT CCT GAT TCC GAA CTA GAC
Asn Ala Asp Pro Ala Leu Asn Trp Gln Tyr Pro Asp Ser Glu Leu Asp

737
AAG CTC AAG GAT CCG GCC ATC AAG ATC TTC TTC TGC GTG AAC CCC AGC
Lys Leu Lys Asp Pro Ala Ile Lys Ile Phe Phe Cys Val Asn Pro Ser

797
AAT CCG CCA TCG GTA AAG ATG GAC GAG CGC AGC CTG GAG CGT GTG CGC
Asn Pro Pro Ser Val Lys Met Asp Glu Arg Ser Leu Glu Arg Val Arg

857
AAG ATT GTG GCA GAG CAT CGA CCG GAT CTG ATG ATC CTG ACC GAT GAC
Lys Ile Val Ala Glu His Arg Pro Asp Leu Met Ile Leu Thr Asp Asp

GTC TAT GGC ACG TTT GCC GAT GGC TTT CAG TCG CTC TTT GCG ATT TGC
Val Tyr Gly Thr Phe Ala Asp Gly Phe Gln Ser Leu Phe Ala Ile Cys

917
CCG GCC AAC ACT TTG TTG GTC TAT TCA TTC TCC AAA TAC TTT GGT GCC
Pro Ala Asn Thr Leu Leu Val Tyr Ser Phe Ser Lys Tyr Phe Gly Ala
```

FIGURE 1C

```
                                          977
ACT GGC TGG CGT CTG GGT GTC GTG GCC GCC CAT AAG GAA AAT ATC TTC
Thr Gly Trp Arg Leu Gly Val Val Ala Ala His Lys Glu Asn Ile Phe

1037
GAC TTG GCA TTG GGC AGG CTG CCT GAG TCC GAG AAA ACA GCG CTC GAT
Asp Leu Ala Leu Gly Arg Leu Pro Glu Ser Glu Lys Thr Ala Leu Asp

1097
GAT CGC TAT CGT TCA CTG CTA CCC GAT GTG CGT TCA TTG AAA TTC CTA
Asp Arg Tyr Arg Ser Leu Leu Pro Asp Val Arg Ser Leu Lys Phe Leu

GAT CGT CTG GTT GCC GAC AGC CGC GCT GTT GCC TTG AAC CAC ACG GCC
Asp Arg Leu Val Ala Asp Ser Arg Ala Val Ala Leu Asn His Thr Ala

1157
GGT CTG TCC ACG CCG CAG CAG GTC CAG ATG ACC TTG TTC TCG TTG TTT
Gly Leu Ser Thr Pro Gln Gln Val Gln Met Thr Leu Phe Ser Leu Phe

1217
GCG CTC ATG GAC GAG AGC GAC CAG TAC AAG CAC ACG CTC AAG CAA CTG
Ala Leu Met Asp Glu Ser Asp Gln Tyr Lys His Thr Leu Lys Gln Leu

1277
ATA CGA CGT CGT GAA GCA ACG CTC TAT CGC GAG TTG GGA ACG CCT CCG
Ile Arg Arg Arg Glu Ala Thr Leu Tyr Arg Glu Leu Gly Thr Pro Pro

1337
CAA AGA GAT GAA AAT GCG GTC GAT TAC TAC ACC TTG ATT GAC CTG CAG
Gln Arg Asp Glu Asn Ala Val Asp Tyr Tyr Thr Leu Ile Asp Leu Gln

GAC GTG ACG TCG AAG CTT TAT GGC GAA GCG TTC TCG AAA TGG GCA GTC
Asp Val Thr Ser Lys Leu Tyr Gly Glu Ala Phe Ser Lys Trp Ala Val

1397
AAG CAG TCC TCG ACC GGC GAC ATG CTG TTC CGG ATT GCC GAC GAA ACA
Lys Gln Ser Ser Thr Gly Asp Met Leu Phe Arg Ile Ala Asp Glu Thr

1457
GGG ATC GTG CTC CTG CCG GGA CGT GGC TTT GGA TCG GAC CGT CCA TCG
Gly Ile Val Leu Leu Pro Gly Arg Gly Phe Gly Ser Asp Arg Pro Ser
```

FIGURE 1D

```
                                      1517
GGA CGC GCC TCC TTG GCC AAT CTC AAC GAG TAT GAG TAC GCG GCC ATA
Gly Arg Ala Ser Leu Ala Asn Leu Asn Glu Tyr Glu Tyr Ala Ala Ile

1577
GGT CGT GCG CTG CGA CAA ATG GCT GAC GAG CTG TAC GCG CAA TAC ACC
Gly Arg Ala Leu Arg Gln Met Ala Asp Glu Leu Tyr Ala Gln Tyr Thr

CAG CAA GGG AAC AAG CGC TGACGGCGAG GGCTTCAAGG CTTACGGCAC
Gln Gln Gly Asn Lys Arg

1637
CGCCAGCCGA AAAAAGCCAG CCCGACCACC AATGCATTGA AAAGAGGCCT CGGCCTCTTT

1697
TCTTGTTTTC CTCTTCACTG AGCCGTCAGG CGTACGAAGT CGCGGTCAAG ATCCTTGATG

1757
GCCGTCTCAA TGCGTTTGCT TCGTTCGGCC GTCCATTGCT CCTCCTGGGC AAGCATTTGC

1817
CTAGAGCGCG CAATCATGCG GGCCATCTCC GCAGGTTGGG GGCCGCCAGC AGTCACACGA 1877                                               1915
TTCTTCACGA TGGCCACAGG GTCCAGCGCT GCCCGGAATT CGAGCTC
```

METHOD AND COMPOSITIONS FOR THE PRODUCTION OF L-ALANINE AND DERIVATIVES THEREOF

SUMMARY OF THE INVENTION

This invention provides an isolated gene, i.e. DNA molecule, encoding aspartate beta decarboxylase. As such, the DNA molecule is free from any nucleotide sequence encoding any other enzymes. The DNA molecule may be inserted into a conventional expression vector such that the DNA molecule is operably linked to an expression control sequence, i.e. containing a promoter, permitting expression of the DNA sequence and production of aspartate beta decarboxylase in a host microorganism transformed with the vector. Typically, the vector contains a selectable marker gene for selection of host cells transformed with the vector; a ribosome binding site permitting translation of the aspartate beta decarboxylase message transcribed from the vector DNA; and, as desired, other genetic elements conventional in this art. A preferred such vector contains as the DNA sequence encoding aspartate beta decarboxylase a sequence identical or substantially identical to the coding region of the DNA sequence depicted in FIG. 1. One vector containing the cloned DNA of FIG. 1 is pPD601, a sample of which has been deposited with the American Type Culture Collection (ATCC) of Rockville, Md. under accession number ATCC 40448 on Apr. 20, 1988.

Naturally, one of ordinary skill in this art could independently clone the gene present in that plasmid using purely conventional means and oligonucleotides designed based on the sequence presented in FIG. 1. For example, aspartate beta decarboxylase genes may be cloned from organisms including *Pseudomycobacteria, Pseudomonas sp., Pseudomonas dacunhae, Clostridium perfingens, Alcaligenes faecalis, Acetobacter sp., Achromobacter sp., Desulfovibrio desulfuricans, Norcardia globerula,* and *Xanthomonas oryzae,* and isolates thereof.

Alternatively, one could readily excise the gene from pPD601 using restriction enzymes selected based on the sequence of FIG. 1, with reconstruction of any lost sequence, if necessary, using synthetic oligonucleotides analogously to the method described hereinafter. As those of ordinary skill in this art will appreciate, the gene may be inserted into any desired expression vector for heterologous expression in microbial host cells.

This invention thus also encompasses a microorganism, preferably *E. coli,* transformed with such a vector, or the progeny of such transformed microorganisms, which are capable of producing aspartate beta decarboxylase Preferably the transformed microorganism or the progeny thereof which produces aspartate beta decarboxylase does so to the substantial exclusion of alanine racemase.

This invention further encompasses a method for producing aspartate beta decarboxylase enzyme to the substantial exclusion of alanine racemase which comprises producing a transformed microorganism, as mentioned above and described in greater detail hereinafter, or progeny thereof, and culturing the microorganism under suitable conditions permitting the production of aspartase beta decarboxylase. The cultured microbial cells may further be lysed or otherwise disrupted and the aspartase beta decarboxylase recovered from cellular debris.

This invention thus provides a composition comprising cells of a microorganism or extracts thereof containing aspartate beta decarboxylase, the composition being characterized by a ratio of aspartate beta decarboxylase activity:alanine racemase activity greater than about 1000. The composition may be immobilized on a support material, preferably further increasing the aspartate beta decarboxylase:alanine racemase activity ration to greater than about 5000, and even more preferably as high as about 25,000, and perhaps even higher.

This invention also encompasses a method for producing L-alanine which comprises contacting a solution containing L-aspartic acid or a salt thereof with a composition as just described, whether immobilized or not, under suitable conditions permitting the conversion of L-aspartic acid or salts thereof to L-alanine. The solution containing L-aspartic acid or a salt thereof may also contain other materials, for example, other amino acids. In that case, the method of this invention produces a mixture enriched in L-alanine.

This invention further encompasses a method for producing a mixture of L-alanine and D-aspartic acid. That method involves contacting a solution of D,L-aspartic acid or a salt thereof with a composition as described above under suitable conditions permitting the conversion of L-aspartic acid or salts thereof in the mixture to L-alanine.

In either of the just mentioned methods, the L-alanine so produced may be isotopically labeled with one or more isotopic atoms selected from the group consisting of $^{14}C$, $^{13}C$, $^{13}N$, $^{15}N$, $^{2}H$, $^{3}H$, $^{17}O$ and $^{18}O$. Such labeling may be conveniently effected using correspondingly labeled L- or D,L-aspartic acid and/or isotopically labeled water.

BRIEF DESCRIPTION OF THE DRAWINGS

FIG. 1. Nucleotide sequence and corresponding amino acid sequence of the aspartate beta decarboxylase gene isolated from *Pseudomonas dacunhae.*

DETAILED DESCRIPTION OF THE INVENTION

The enzyme aspartate beta decarboxylase (aspartate 4-decarboxylase, aspartate 4-carboxylyase, E.C. 4.1.1.12) catalyzes the removal of the beta carboxyl group from L-aspartate with complete retention of the asymmetric center to produce L-alanine. The enzyme activity has been detected in several types of microorganisms.

Aspartate beta decarboxylase is useful in the production of L-alanine from L-aspartate. However, as described earlier, there are two main drawbacks to current methods involving the production of aspartate beta decarboxylase from wild-type microorganisms, and its subsequent use in the production of L-alanine. First, the level of enzymatic activity produced by the microorganisms known in the art is relatively low, leading to biocatalysts with less than desired potency for producing L-alanine. The second drawback is the presence in current strains of the undesired enzyme alanine racemase at levels high enough to cause some loss in optical purity of the L-alanine product. Presently, the cells must be subjected to special pretreatments prior to use as a biocatalyst in order to selectively inactivate the alanine racemase enzyme. Clearly, new methods for the production of cells containing aspartate beta decarboxylase at much higher activity levels, and to the substantial exclusion of alanine racemase without the need for special pretreatments prior to catalytic use would be desirable. Accordingly, work leading to the present invention, including the isolation of a nucleic acid sequence (cloning of the gene) encoding aspartate beta decarboxylase was undertaken.

The general procedure by which the cloning of the aspartate beta decarboxylase gene can be accomplished is through the isolation of a DNA fragment encoding the polypeptide carrying the aspartate beta decarboxylase activity from a suitable donor microorganism, and incorporating the DNA fragment into a suitable vector, of which many are known in the art. Suitable donor microorganisms include all microorganisms carrying a gene encoding a polypeptide which catalyzes the decarboxylation of L-aspartate to L-alanine. Specific examples of such microorganisms include *Pseudomycobacteria, Pseudomonas sp., Pseudomonas dacunhae, Clostridium perfringens, Alcaligenes faecalis, Acetobacter sp., Achromobacter sp., Desulfovibrio desulfuricans, Norcardia globerula*, and *Xanthomonas oryzae*. However, it will undoubtedly be possible for the skilled microbiologist to find other examples of wild-type strains capable of producing aspartate beta decarboxylase.

Suitable cloning vectors useful in the practice of this invention normally contain an origin of replication and a selectable marker to maintain the stability of the vector in the host cell and to facilitate the identification of transformants. A description of some methods and materials useful in the cloning of the aspartate beta decarboxylase gene can be found in *Molecular Cloning: A Laboratory Manual* [T. Maniatis, E. Fritsch, and J. Sambrook, Cold Spring Harbor Laboratory (1982)] and references therein, which are hereby incorporated by reference. Any of the strategies and methods known in the art for obtaining a clone of a gene may be used in accord with this invention.

As an example of a preferable method for obtaining a clone of the gene encoding aspartate beta decarboxylase, the following steps were carried out. First the enzyme was purified to homogeneity from cell paste of a strain of the genus Pseudomonas by applying a combination of physical separation steps, chromatographic separation methods, ammonium sulfate precipitation, and finally HPLC purification. The aspartate beta decarboxylase so produced was judged as pure by polyacrylamide gel electrophoresis, exhibiting a single band of an apparent molecular weight of approximately 50,000 Daltons. The purified enzyme was then partially sequenced by digesting the enzyme with trypsin, isolating the tryptic fragments by HPLC, and determining the sequence of one or more of the fragments using an Applied Biosystems gas phase protein sequencer. The N-terminal amino acid sequence of the protein was also determined using the undigested purified protein.

As a next step, using purely conventional methods, oligonucleotide probes were synthesized corresponding to regions of the protein sequences giving rise to a relatively low degeneracy, and these oligonucleotide sequences were made radioactive by phosphorylation with radioactive phosphate. The radioactive oligonucleotide probes were then used to screen a library of genomic DNA prepared by digesting chromosomal DNA from a donor microorganism of the genus Pseudomonas with the restriction endonuclease Sau3A. Following size fractionation of the partially digested DNA to purify fragments in the size range of 10–12 kilobases, the fragments were ligated into a BamHI restriction site of an *E. coli* plasmid vector containing a gene for resistance to ampicillin, and resulting circularized DNA was used to transform an *E. coli* host strain. Colonies appearing after 18 hour growth in the presence of ampicillin were replica-plated onto nitrocellulose filters and the filters containing the immobilized DNA were probed with the radioactive synthetic oligonucleotides under standard hybridization conditions. Colonies hybridizing with the oligonucleotide probes were cultured, and plasmid DNA was prepared from these colonies. The DNA was digested with several restriction endonucleases, fractionated on an agarose gel, and blotted onto nylon filters. Those clones hybridizing to two different probes were subcloned into *E. coli* plasmid vectors, and shown by DNA sequencing to contain an open reading frame corresponding to a polypeptide of molecular weight approximately 50,000. This polypeptide also contained regions of sequence matching exactly the sequences determined from the originally purified protein. The extracts from these cells were shown by assay to have aspartate beta decarboxylase activity.

The DNA fragment encoding the polypeptide displaying aspartate beta decarboxylase activity was then expressed. The general strategy for expression of the aspartate beta decarboxylase gene involves the ligation of the DNA fragment encoding the polypeptide displaying aspartate beta decarboxylase activity into an expression vector suitable for the desired host cell, many examples of which are well known in the art. Suitable expression vectors are normally characterized by the presence of an origin of replication, a promoter or other transcription enhancing sequences, a ribosome binding site or Shine-Dalgarno sequence, and a transcriptional termination sequence. The expression vector may also include a gene conferring resistance to an antibiotic as a selectable marker; however, plasmids containing any other gene encoding a protein required by the host microorganism for growth and viability may be used as a selectable marker, if desired. Promoters commonly used in recombinant DNA constructions include tryptophan, alkaline phosphatase, beta-galactosidase, beta-lactamase, and $P_L$ promoter systems; and hybrid promoter systems composed of components or structures from two or more known promoter systems such as tac. While these are the most common promoters used in bacterial host strains, other strains and microbial species amenable to genetic manipulation and other promoters useful in those host strains may also be used. After the ligation, the resultant vector of this invention contains the aspartate beta decarboxylase gene in operative association with a promoter such that host cells transformed with the vector are capable of directing the production of aspartate beta decarboxylase.

In a preferred embodiment of this invention, the host strain for expression of the aspartate beta decarboxylase gene is *E. coli*, and the promoter system is selected from the group consisting of alkaline phosphatase, beta-lactamase, $P_L$, lac, trp, and tac promoters. Expression of the gene is thus accomplished by ligation of the gene into a vector for gene expression in the chosen host strain. In an especially preferred embodiment of this invention, the vector used for the expression of the aspartate beta decarboxylase gene in *E. coli* is pBR322 or a plasmid which is derived from pBR322. The plasmid pBR322 contains genes encoding ampicillin and tetracycline resistance, allowing the facile identification of transformed cells. The DNA sequence encoding the aspartate beta decarboxylase gene was incorporated into the expression vector pAL181 (derived from pBR322 and deposited and accessible under the ATCC no. 40134). The expression vector pAL181 is described in the published International Application WO 86/01540, and may be used for the expression of aspartate beta decarboxylase after insertion of the coding sequences of the aspartate beta decarboxylase gene. Induction of the synthesis of aspartate beta decarboxylase is accomplished by a temperature shift from 30°-40° C. The aspartate beta decarboxylase enzyme is produced at levels of from about 5% to about 40% of the total protein in the cell, thus yielding a crude enzyme-containing composition with very high aspartate beta decarboxylase activity. Also important is the fact that the aspartate beta decarboxylase enzyme is produced to the substantial exclusion of the alanine racemase activity. By "producing aspartate beta decarboxylase to the substantial exclusion of alanine racemase" is meant the production in cells, or extracts derived therefrom, of aspartate beta decarboxylase enzymatic activity relative to alanine racemase at levels high enough such that L-alanine is produced in at least 99% optical purity and without the need for inactivation of any alanine racemase. Typical ratios of aspartate beta decarboxylase: alanine racemase activity consistent with the term "substantial exclusion", expressed as the ratio of activities in International units, are in the range of from about 500 to about 1000, and can be much higher. Preferably the ratio is in the range of from about 1000 to about 3000. This is compared with corresponding ratios in the wild-type cells of approximately 25-40.

It should be noted that other vectors known in the art, whether applicable in bacterial or fungal host strains, may be used in the practice of this invention, provided that aspartate beta decarboxylase enzyme is produced at a large excess relative to alanine racemase. It is also not critical whether the expression of the gene results in enzyme produced intracellularly or extracellularly, since the desired product may be conveniently recovered and, if desired, further purified in either case.

An important application for the cells produced according to the present invention containing aspartate beta decarboxylase activity in high levels and to the substantial exclusion of alanine racemase is in the production of L-alanine. In accord with the practice of this invention, the cells producing high relative levels (as previously described) of aspartate beta decarboxylase enzyme may be contacted with a solution containing a source of L-aspartate, with the resulting conversion of at least a portion of the L-aspartate in the reaction mixture to L-alanine. The cells may be permeabilized to facilitate diffusion of the substrates and products into and out of the cells. Aspartate beta decarboxylase may also be added to the L-aspartate-containing reaction mixture in the form of cell extracts containing crude, partially purified, or purified aspartate beta decarboxylase enzyme. The reaction is carried out in similar fashion by contacting the cell extracts with a solution containing L-aspartate, resulting in the conversion of at least a portion of the L-aspartate in the reaction mixture to L-alanine.

The aspartate beta decarboxylase-containing cells, or extracts derived therefrom, may also be immobilized, if desired. Immobilization methods which may be used in the practice of this invention include well-known methods such as entrapment in polymeric gels, covalent attachment, crosslinking, adsorption, and encapsulation. Some examples of these methods are described by A. M. Klibanov in *Science*, 219:722-727 (1983) and the references therein and in *Methods in Enzymology*, volume 44, (K. Mosbach editor) which are hereby incorporated by reference. In a preferred embodiment, a support material containing at least 20% by weight of silica or alumina is contacted with aminoalkyl compound such as an aminoalkyl silane, polyethyleneimine, or a polyalkylamine, followed by activation with glutaraldehyde. The enzyme-containing solution is then contacted with the activated support to produce an immobilized enzyme composition having aspartate beta decarboxylase activity to the substantial exclusion of alanine racemase and being useful in the conversion of L-aspartate to L-alanine. Other immobilization supports useful in the practice of this invention include porous glass and porous ceramics, bentonite, diatomaceous earth, charcoal, sepharose and sepharose derivatives, cellulose and cellulose derivatives, polyacrylamide and polyacrylamide derivatives, polyazetidine, alginate, carrageenan, chromosorb, and the like. The skilled artisan will appreciate that a number of other materials suitable for the immobilization of cells or extracts derived therefrom may also be useful for the immobilization of the aspartate beta decarboxylase of the present invention. These supports can be activated, if desired, by techniques well-known in the art.

An additional aspect of this invention, novel and unexpected, is that the aspartate beta decarboxylase: alanine racemase ratio can be further enhanced upon immobilization of the enzyme. Whereas the aspartate beta decarboxylase: alanine racemase ratio may be of the order of about 1000 in the cells or extracts produced therefrom in accordance with this invention, the ratio has been found to increase substantially after immobilization. By carrying out the immobilization under conditions in which the aspartate beta decarboxylase retains a higher fraction of its catalytic activity after immobilization than does the alanine racemase, the aspartate beta decarboxylase: alanine racemase ratio has been increased to the range of from about 5000 to about 25,000. Examples of such modified conditions include, but are not restricted to, the addition of 2-ketoglutarate and/or pyridoxal phosphate to the enzyme solution prior to immobilization; varying the pH of the immobilization reaction, varying the temperature under which the immobilization is carried out, and the like. This allows the production of L-alanine in essentially an optically pure state, with levels of D-alanine, if any, less than the limits of detection in the assay.

The reaction to produce L-alanine utilizing cells containing aspartate beta decarboxylase, or compositions comprising extracts derived from said cells, is carried out by contacting a solution containing L-aspartate with the aspartate beta decarboxylase under conditions permitting the conversion of at least a portion of the L-aspartate to L-alanine. The concentration of L-aspartate is not critical in this reaction. The enzymatic reactions of this invention are carried out at temperatures in the range of from about 4° C. to about 90° C., and preferably at temperatures ranging from about 20° C. to about 60° C. The optimal pH for the reaction ranges from about 2.0 to about 12.0, and more preferably from about 4.0 to about 9.0. The cofactor pyridoxal phosphate is required for full enzymatic activity, and although the enzyme binds pyridoxal phosphate tightly, it is desirable to add exogenous cofactor to the reaction mixture. Pyridoxal phosphate is preferably added to the reaction mixture at a concentration ranging from about 0.005 millimolar to about 2.5 millimolar. A 2-ketoacid may also be added to the reaction mixture, if desired. Any of a number of different 2-ketoacids may be used in accord with this invention. Those ketoacids particularly useful in the practice of this invention correspond to a naturally occurring amino acid or compounds similar in structure to naturally occurring amino acids; the ketoacids may be added in the free acid form, or as a salt of any positively charged ion. Some examples of 2-ketoacids useful in the practice of this invention are glyoxylate, pyruvate, 2-ketobutyrate, 2-ketopentanoate, oxaloacetate, 2-ketoglutarate, 2-ketoadipate, phenylpyruvate, 2-ketoisovalerate, 2-ketoisopentanoate, and the like. The 2-ketoacids are added to the reaction medium at a concentration ranging from about 0.05 to about 10.0 millimolar.

The aspartate beta decarboxylase compositions of this invention can thus be used for the efficient production of L-alanine. As an example, a two milliliter sample of a ceramic-containing support material to which was bound 60 milligrams of a cell extract containing aspartate beta decarboxylase derived from a recombinant *E. coli* was contacted with 0.5 liter of a solution of 1.5 M L-aspartate. The solution contained pyridoxal phosphate added to a concentration of 0.10 mM and 2 ketoglutarate added to a concentration of 1 mM. The pH of the reaction mixture was maintained at 5.5. After 36 hours the aspartate had been completely converted to L-alanine. The productivity of the biocatalyst was calculated to be 927 gram L-alanine produced per liter of catalyst bed volume per hour.

The process is equally applicable to the production of mixtures containing D-aspartate and L-alanine by the action of the aspartate beta decarboxylase on D,L-aspartate. In this embodiment, the aspartate beta decarboxylase composition catalyzes the decarboxylation of only the L-aspartate in the racemic D,L mixture. The D-aspartate in the mixture is neither a substrate nor an inhibitor. The resulting product is a 1:1 mixture of D-aspartate and L-alanine. The D-aspartate and L-alanine may be separated and recovered by methods known in the art, or the D-aspartate/L-alanine mixture may be recovered or used directly as a mixture. The aspartate beta decarboxylase compositions of this invention are further applicable to the production of L-alanine or L-alanine/D-aspartate mixtures containing radioactive or non-radioactive isotopic labels. Such products are produced simply by using an appropriately labelled aspartate precursor, and/or by carrying out the reaction in the presence of isotopically labelled solvent. Examples of isotopic labels which can be incorporated into the L-alanine and /or D-aspartate products are 14-C, 13-C, 13-N, 15-N, 2-H, 3-H, 17-O, 18-O, and the like.

The invention will now be further illustrated by the following examples, which are given here for illustrative purposes only and are not intended to, and should not be construed to, limit the scope of the invention.

EXAMPLES

Example 1: Purification and Sequencing of Aspartate Beta Decarboxylase

During the course of the purification, aspartate beta decarboxylase activity was assayed by the following procedure. An aliquot of enzyme sample (0.1–0.5 ml) was added to 0.9–0.5 ml of a solution containing sodium acetate (0.1 M), L-aspartic acid (0.1 M), pH 5.5, and the reaction mixture was incubated at 20° C. Aliquots of 0.020 ml were removed over a 30 minute time period and diluted to 1 ml by addition of a reagent solution prepared according to the following composition: 2 ml of a 50 mg/ml solution of L-amino acid oxidase, 0.5 ml of a 2 mg/ml solution of horse radish peroxidase, 2.5 ml of a 15 mg/ml solution of 4-aminoantipyrine, 5 ml of a 2 mg/ml solution of 2,4-dichlorophenol, and 89 ml of Tris citrate buffer, pH 7.5. The ensuing reaction in the diluted aliquot was allowed to proceed for 10 minutes and was stopped by the addition of 0.050 ml of a 10% solution of sodium dodecyl sulfate (SDS). The absorbance of the reagent solution is read at 495 nm, and the L-alanine concentration is determined by calculation from a standard curve prepared the same day.

A strain of *Pseudomonas dacunhae* (ATCC 21192), which is publicly available and listed in the general ATCC catalog, was cultured in a medium containing, per liter, Bactotryptone (10 g), yeast extract (5 g), sodium chloride (5 g), 1 molar ammonium fumarate (37.6 ml), 1 molar sodium fumarate (73.5 ml), NZ amine (2 g), potassium dihydrogen phosphate (0.5 g), magnesium phosphate (0.05 g). The cells were grown aerobically overnight, and collected by centrifugation.

The cell paste harvested from 10 liters of growth media was suspended in three volumes of a buffer containing 50 mM potassium phosphate, 0.2 mM pyridoxal phosphate, and 1 mM 2-ketoglutarate, 1 mM EDTA disodium, 0.2 mM dithiothreitol, pH 6.8. The cells were disrupted using a Manton-Gaulin homogenizer, the cell debris was removed by centrifugation (Sorvall, 9000 rpm), and the supernatant was subjected to a heat treatment at 50° C. for one hour. The precipitated proteins were removed by centrifugation (Sorvall, 9000 rpm), and the supernatant was loaded onto a DEAE-Sephadex column (4.5×10 cm) equilibrated with 0.1M potassium phosphate buffer, pH 6.8. The column was eluted at a flow rate of 1 ml/minute with 0.1M potassium phosphate buffer, then 0.14M potassium phosphate buffer, and finally with a linear gradient of potassium phosphate buffer between 0.14 and 0.33M, pH 6.8. The fractions containing aspartate beta decarboxylase activity were concentrated 6-fold in an Amicon diafiltration device (YM-10 membrane), and loaded onto a Sephacryl S-200 column (2.5×50 cm) pre-equilibrated with 50 mM potassium phosphate buffer, pH 6.8 and eluted with 50 mM potassium phosphate buffer, pH 6.8 containing 0.2 mM pyridoxal phosphate and 1 mM 2-ketoglutarate. The fractions containing aspartate beta decarboxylase activity were pooled and concentrated 4-fold in an Amicon diafiltration device (YM-10 membrane). At this stage, polyacrylamide gel electrophoresis showed the enzyme to consist principally of two bands, one of apparent molecular weight 90,000 and one of apparent molecular weight 50,000. The proteins corresponding to these two bands on the gel were resolved by selective precipitation with ammonium sulfate (0–60% saturation and 60–100% saturation). The material precipitated in the 60–100% fractionation contained only the protein corresponding to the band of apparent molecular weight 50,000, and displayed high aspartate beta decarboxylase activity. The two proteins were resolved for sequencing on reversed-phase HPLC using a linear gradient between 0.1% trifluoroacetic acid (TFA) in water and 0.1% TFA in 95% aqueous acetonitrile. The fraction containing the approximately 50,000 Dalton protein was evaporated to dryness and stored at 4° C. until ready to be sequenced.

The sequencing was carried out on an Applied Biosystems protein sequencer. The native protein purified to homogeneity as just described was sequenced to obtain the amino acid sequence at the N-terminus of the protein; in addition, fragments of the protein were produced by conventional digestion with trypsin, the fragments were isolated on reversed-phase HPLC, and the sequences of two independent tryptic fragments were similarly determined. The amino acid sequences determined are given below.

N-Terminal Amino Acid Sequence

SerLysAspTyrGlnSerLeuAlaAsnLeuSerProPheGluLeuLysAspGluLeuIleLys IleAlaSerGlyAspGlyAsnArgLeuMetLeuAsnAlaGlyArgGlyAsnProAsnPheLeuAla Thr

Amino Acid Sequence Of Isolated Tryptic Fragments

IleGlyMetProValPheThrProTyrIleGluIleProGluLeuAlaGlnTyrALaLeuGlu GluValAlaIleAsnAla

AlaSerLeuAlaAsnLeuAsnGluTyrGluTyrAlaAlaIleGlyArg

Example 2: Cloning of the Gene Encoding Aspartate Beta Decarboxylase

From the determined amino terminal peptide sequence, all possible DNA sequences encoding a given amino acid sequence were determined. A 17 nucleotide DNA probe was synthesized corresponding to the region of the protein sequence having a 256-fold degeneracy. A 32-fold degenerate oligonucleotide corresponding to amino acid sequence from one of the internal tryptic fragments was similarly identified and synthesized. Thus, single-stranded oligonucleotide probes having the following DNA sequences were synthesized and purified by standard means. The sequences for the two probes are shown below.

5'-*GGNAAYCCNAAYTTYYT*-3'

5'-*AAYGARTAYGARTAYGC*-3'

Y=T or C
R=A or G
N=A, G, C, or T

These oligonucleotides were radioactively labelled at the 5'-ends by incubation with T4 polynucleotide kinase in the presence of gamma-$^{32}$P-ATP according to the manufacturer's instructions. The radiolabelled oligonucleotide probes were then used to screen a library of genomic *P. dacunhae* DNA for sequences complementary to that of the probes. The *P. dacunhae* library was prepared by the method described below.

A fresh one liter culture of *P. dacunhae* was grown to mid-log phase in L-broth medium at 37° C. The cells were harvested by centrifugation, washed once with 50 mM Tris HCl buffer, pH 8.0, containing 10 mM EDTA, and resuspended in 50 ml of the same buffer. Fresh lysozyme was added to a final concentration of 1 mg/ml, and the solution was incubated for 30 minutes at 30° C. The cells were rapidly frozen followed by immediate thawing. Sodium dodecylsulfate was added to a final concentration of 1% (w/v); ribonuclease A was added to a final concentration of 10 microgram/ml; the resulting solution was incubated for 30 minutes at 30° C. Proteinase K was then added to 50 microgram/ml final concentration, and the 30° C. incubation was continued for an additional 2 hours. An equal volume of chloroform/isoamyl alcohol solution (24:1) was then added. Following complete mixing, the resulting solution was subjected to centrifugation at 10000 g for 10 minutes to separate the organic and aqueous phases. The aqueous phase was decanted into a fresh vessel, avoiding the transfer of particulate matter, and ammonium acetate was added to a 2.5M final concentration, followed by the addition of isopropanol to a final concentration of 36% v/v. Chromosomal DNA was precipitated from the solution, collected by centrifugation, and washed twice with a solution of 70% aqueous ethanol. After air drying, the DNA was resuspended in 20 ml of 10 mM Tris HCl buffer, pH 8.0, containing 1 mM EDTA. A portion of the DNA was further purified by ultracentrifugation in the presence of cesium chloride and ethidium bromide solutions as described in *Molecular Cloning: A Laboratory Manual* [T. Maniatis, E. Fritsch, and J. Sambrook, Cold Spring Harbor Laboratory (1982)].

A library of *P. dacunhae* genomic DNA was prepared by digesting 150 micrograms of chromosomal DNA prepared as described above with 10 units of the restriction endonuclease Sau3A for 15 minutes at 37° C. in order to generate a random collection of DNA fragments averaging 10–12 kilobase pairs in length. Following size fractionation by gel electrophoresis to purify the 10–12 kilobase-sized fragments, the genomic fragments were ligated to an *E. coli* plasmid vector containing a gene for resistance to ampicillin, that had previously been linearized by digestion with the restriction endonuclease BamHl and dephosphorylated with calf intestinal alkaline phosphatase. The resulting circularized DNA was used to transform *E. coli strain* MM294 to ampicillin resistance. Approximately 12000 colonies appearing after 18 hour growth on L-broth agar plates in the presence of 100 microgram/ml of ampicillin were transferred onto nitrocellulose filters. DNA from the individual colonies was immobilized onto the filters by successive treatments with 1) 10% SDS w/v for 3 minutes; 2) 0.5M NaOH, 1.5M NaCl; 3) 0.5M Tris HCl buffer, pH 7.5, containing 1.5 M NaCl for 5 minutes; 4) baking in a vacuum oven at 80° C. for 2 hours at 80° C. After immobilization of the DNA, the filters were washed in 0.15M NaCl, 0.015M sodium citrate containing 0.2% SDS for 10 minutes, followed by pretreatment with a hybridization solution of 3M tetramethyl ammonium chloride (TMAC), 10 mM sodium phosphate, pH 6.8, 1 mM EDTA, 0.6% SDS, and and Denhardt solution according to the method of Jacobs et al [*Nature* 313, 806–810 (1985)]. Forty picomoles of radiolabelled oligonucleotide probe derived from the N-terminal amino acid sequence was added to the hybridization solution, and filters containing the immobilized DNA were incubated with the hybridization mixture containing the probes at 48° C. for 24 hours. Following removal of unbound radiolabelled material, an autoradiographic exposure was made, and colonies corresponding to positive signals were replated to obtain single colony isolates These isolates from the original screening were reprobed with the same radiolabelled oligonucleotide to confirm positives. Plasmid DNA was prepared from these colonies and analyzed by restriction endonuclease digestion followed by Southern blot analysis to identify smaller DNA fragments that hybridized to a radiolabelled oligonucleotide corresponding to one of the internal tryptic fragment amino acid sequences. Those plasmid DNA isolates which hybridized to both oligonucleotide probes were chosen as the best candidates to contain full-length clones of the gene corresponding to aspartate beta decarboxylase. Ampicillin resistant transformants of *E. coli* strain MM294 carrying the doubly-positive plasmids were cultured overnight in L-broth medium containing ampicillin. The cells were harvested by centrifugation, and the extracts from these cells were shown by assay to have measurable aspartate beta decarboxylase activity, albeit at low levels.

Plasmids that conferred aspartate beta decarboxylase activity were shown by digestion with restriction endonucleases to contain a DNA fragment of approximately 11000 base pairs in length. Subcloning of specific restriction fragments from this initial plasmid identified a 3.4 kilobase Sau3A/EcoRl DNA fragment which hybridized to both probes and conferred aspartate beta decarboxylase activity on strains carrying plasmids bearing this fragment. Sequencing of a 2018 base pair DNA fragment showed a single open reading frame of 1599 nucleotides. Translation of this open reading frame identified three regions, one at the amino terminus and two internal sequences, which matched exactly the protein sequence which had been determined by amino acid sequencing of the purified protein The full-length sequence for the gene encoding aspartate beta decarboxylase, and its translated amino acid sequence are shown in FIG. 1.

Example 3: Expression of the P. dacunhae asdA Gene, Encoding Aspartate Beta Decarboxylase The asdA gene encoding aspartate beta decarboxylase was expressed in *E. coli* under the regulated control of the $P_L$ promoter from the *E. coli* bacteriophage Lambda.

Plasmid pAL781 is derived from pAL181, previously described in the published International Patent Application WO 86/01540 and deposited with the ATCC under the accession number 40134, by the addition of a transcriptional termination sequence from the aspA gene of *E. coli* inserted between the unique PstI and HindIII sites of pAL181. Plasmid pAL781 thus contains an origin of replication and a beta-lactamase gene for propagation in strain GI400 during growth on ampicillin-containing medium, the $P_L$ promoter, a "Shine-Delgarno" sequence for enhancing translation derived from the CII gene of Lambda, and the aspA transcription termination element.

To express the asdA gene from the $P_L$ promoter of plasmid pAL781, the plasmid pPD761 was constructed as follows. Plasmid pAL781 was digested with the enzyme KpnI and treated with the large fragment of DNA Polymerase I to remove the single-stranded DNA ends generated by KpnI treatment. The plasmid was then digested with the enzyme PstI, and the resulting linearized DNA molecule was purified by agarose gel electrophoresis. The linearized PAL781 DNA contains a blunt end immediately after the sequence ATG on the non-coding DNA strand which will provide the initiator methionine codon and contains the single stranded DNA sequence 5'-TGCA-3' on the coding strand. Plasmid pPD601, which contains the entire asdA gene, was digested with the enzymes SacI and NsiI and the resulting 1.6 Kb DNA fragment was purified by agarose gel electrophoresis The NsiI site is located 3' to the open reading frame encoding aspartate beta decarboxylase. The SacI site is within the coding region of the asdA gene; therefore, the SacI/NsiI fragment is missing DNA sequences encoding the first 15 amino acids of aspartate beta decarboxylase. To provide these missing sequences, complimentary oligonucleotides were synthesized on an Applied Biosystems DNA synthesizer. The oligonucleotides extended from nucleotide +4 of the asdA open reading frame to the SacI site. Upon hybridization, the two oligonucleotides form a double stranded DNA molecule with a blunt end that begins with the second codon of the asdA gene and single stranded end that is complimentary to a SacI site. A three part ligation was performed with the KpnI/-PolI/PstI generated pAL781 DNA fragment, the 1.6 Kb SacI/NsiI fragment of asdA, and the double stranded blunt/SacI oligonucleotide. The single stranded region of the NsiI site will hydridize to the single stranded region of the PstI site. The resulting circularized molecule contains the asdA gene now regulated by the $P_L$ promoter. Strain GI400 was transformed to ampicillin resistance with a portion of the product of the ligation reaction.

Ampicillin resistant colonies from the above transformation reaction were isolated and DNA was prepared from the cells. Restriction endonuclease digestion identified plasmids that had the structure expected for a plasmid containing the asdA gene under the control of the $P_L$ promoter. DNA sequencing identified those plasmids that contained the open reading frame for the asdA gene beginning with an initiator methionine codon ATG and extending through the SacI site. The resulting expression plasmid, pPD761, was then assayed for its ability to produce aspartate beta decarboxylase.

GI400 cells, an *E. coli* strain characterized by the insertion of the lambda immunity region into the lacZ gene, carrying pPD761 were grown at 30° C. in liquid medium containing ampicillin to an optical density of A550=1.0. Expression of the asdA gene was induced by shifting the temperature of the culture to 40° C. Aliquots were removed at various times thereafter up to six hours post induction. The presence of aspartate beta decarboxylase was analyzed by SDS polyacrylamide gel electrophoresis (SDS/PAGE) of total cellular proteins. At the time of induction, little or no aspartate beta decarboxylase protein was visible by SDS/PAGE analysis. However, within 30 minutes after shifting the temperature of the culture to 40° C., a new protein band appears on SDS/PAGE which comigrates with purified aspartate beta decarboxylase protein. The newly synthesized aspartate beta decarboxylase accounts for approximately 20% of the total cellular proteins. An aliquot of the cells expressing asdA was also analyzed for aspartate beta decarboxylase enzymatic activity. At the time of induction, no measurable aspartate beta decarboxylase activity was observed in cell extracts; whereas by thirty minutes post induction, significant amounts of aspartate beta decarboxylase activity were found in the soluble portion of total cell extracts. After two hours induction, the specific activity of the total cellular proteins for aspartate beta decarboxylase activity was 20 International units per milligram of soluble protein.

Example 4. Alternative Expression of the asdA Gene

Plasmid pPD722 was constructed by ligating the 1.9 Kb XmnI/XbaI fragment of pPD601 to plasmid pAL181 which had been digested with NsiI, treated with large fragment of DNA Polymerase I to blunt the ends and then digested with XbaI. The resulting plasmid, approximately 4.8 Kb in size, contains the asdA gene transcriptionally regulated by the pL promoter in a fashion similar to that described in Example 3 for plasmid pPD761. However, "Shine/Delgarno"like sequences 5' to the asdA initiator methionine and a putative transcription termination element 3' to the asdA open reading frame are from the original DNA fragment encoding the asdA gene of *P. dacunhae.*

Plasmid pPD722 was introduced into *E. coli* strain GI400, selecting for ampicillin resistance. Aspartate beta decarboxylase synthesis and enzymatic activity were measured as described in Example 3. Two hours after induction, newly synthesized aspartate beta decarboxylase comprises approximately 25% of the total soluble protein with specific activity of 20 International units per milligram of soluble cell extract.

Plasmids pPD734 and pPD741 were also examined. These plasmids were derived from pPD722 and pAL781. Plasmid pPD734 contained the aspA transcription termination element along with the asdA "Shine/Delgarno" sequence from translation initiation; whereas pPD741 utilized the asdA putative transcription termination element along with CII "Shine/Delgarno" sequence from pAL781. In all cases examined, aspartate beta decarboxylase specific activity of 20 International units per milligram of soluble cell extract or higher was obtained.

Example 5: Immobilization of Cells Containing Aspartate Beta Decarboxylase To The Substantial Exclusion of Alanine Racemase Cells expressing aspartate beta decarboxylase at high levels produced according to Example 4 were harvested by centrifugation. The cell paste (1 kg) is suspended in 0.5 liters of potassium phosphate buffer (0.1M, pH 6.8) containing pyridoxal phosphate (0.5 mM) and pyruvate (2.5 mM) (hereafter referred to as standard buffer) and the cell suspension is cooled to 4° C. A monomer solution (0.5 kg) of acrylamide: dimethylaminoethyl methacrylate: N,N-methylenebisacrylamide in the ratio of 85.5:9.5:5.0 respectively (w/w) is added to the cell suspension, and the polymerization is initiated by the addition of 50 ml of 10% (v/v) beta-dimethylaminopropionitrile and 50 ml of 10% (w/v) ammonium persulfate. The polymerization reaction starts after about 3-5 minutes, and the temperature during the exothermic polymerization process is maintained at approximately 30° C. After polymerization is complete, the gel is removed from the reactor and cut into pieces of approximately 1-2 millimeters in diameter. After washing the immobilized cells with standard buffer, the product is stored at 4° C. until ready for use.

Example 6: Alternative Immobilization of Cells Containing Aspartate Beta Decarboxylase

*E. coli* cells prepared according to Example 3 were immobilized by the polyazetidine method described by Wood and Calton in U.S. Pat. No. 4,436,813. Accordingly, 50 grams of cell paste was mixed with 50 grams of Polycup 172 (Hercules Chemical, USA) and the resulting mixture was distributed onto 750 grams of molecular sieves at 25° C. and a pressure of 20 Torr. for 45 minutes. After further drying overnight at room temperature, the resulting coated molecular sieves containing immobilized aspartate beta decarboxylase were stored at 4° C. until ready for use.

Example 7: Alternative Immobilization of *E. coli* containing Aspartate Beta Decarboxylase The procedure of Example 6 was repeated except that Amberlite IRA 938 resin was used in place of the molecular sieves. The immobilized biocatalyst could be stored at 4° C. until ready for use if desired.

Example 8: Immobilization of *E. coli* containing Aspartate Beta Decarboxylase in Carrageenan Gels Cells of recombinant *E. coli* produced as in Example 4 were immobilized by the procedure of Chibata et al [*Applied Biochem. and Biotechnol.* 13, 231-240 (1986)]. Accordingly, one kilogram of *E. coli* cells containing high levels of aspartate beta decarboxylase was suspended in one liter of physiological saline at 40° C. Simultaneously, 0.184 kg of kappa-carrageenan was dissolved in 3.75 liters of physiological saline at 45° C. The two solutions were combined and thoroughly mixed, and the resulting mixture was cooled to 10° C. After treatment of the gel with 0.3M potassium chloride, the resulting stiff gel was cut into small pieces with a knife. The immobilized cells could be used in this form, or subjected to further hardening by treatment with glutaraldehyde and hexamethylenediamine prior to use.

Example 9: Immobilization of Cell Extracts Containing Aspartate Beta Decarboxylase Activity to the Substantial Exclusion of Alanine Racemase An amine-activated silica support material (0.8 g) was treated with 10 ml of a solution of glutaraldehyde (5% w/v) in 0.1M potassium phosphate buffer, pH 6.8 for 1 hour. The glutaraldehyde solution was removed, and the support was washed by flushing with potassium phosphate buffer until no glutaraldehyde could be detected in the effluent with 2,4-dinitrophenylhydrazine. Three separate immobilization reactions were carried out using 20 ml solutions of 0.1M potassium phosphate buffer containing pyridoxal phosphate (0.5 mM), 2-ketoglutarate (2.5 mM), and aspartate decarboxylase enzyme prepared by disruption of recombinant *E. coli* cells as in Example 4 and removal of the cell debris by centrifugation (66 mg). The pH of the solution was adjusted to 6.0 with hydrochloric acid. The enzyme-containing solutions were recirculated through the support until no further uptake of enzyme was detected by both protein and activity assay of the supernatant, and immobilized enzyme was then washed with 0.3M NaCl in potassium phosphate buffer containing pyridoxal phosphate and 2-ketoglutarate. The immobilized enzyme was assayed for activity, and the result is shown below.

| Immobilization of Aspartate Beta Decarboxylase | |
| --- | --- |
| Protein Offered | 77 mg |
| Activity Offered (units) | 850 |
| Protein Bound | 69 mg |
| Activity Bound | 790 |

Example 10: Alternative Immobilization of Aspartate Beta Decarboxylase

One hundred grams of aminopropyl silica (Corning) was suspended in 250 ml of a 5% w/v solution of glutaraldehyde in potassium phosphate buffer (50 mM, pH 7.0). The mixture was mixed on an orbital shaker for 60 minutes at 20° C., and the activated silica particles were collected by filtration, washed exhaustively with reaction buffer until no glutaraldehyde could be detected in the washings by reaction with 2,4-dinitrophenylhydrazine. The support was then suspended in a solution of 500 ml of 50 mM potassium phosphate buffer, pH 6.8, containing pyridoxal phosphate (2.5 mM), 2-ketoglutarate (5 mM), and aspartate beta decarboxylase prepared as in Example 9 (5 grams). The suspension was mixed on an orbital shaker for 2 hours, and the immobilized enzyme was collected by filtration and washed with reaction buffer followed by reaction buffer containing 0.3M NaCl, and finally with reaction buffer again. The immobilized enzyme was stored damp at 4° C. until ready for use.

Example 11: Immobilization of Aspartate Beta Decarboxylase on Chitosan

One gram of chitosan particles, produced by dripping an aqueous solution of chitosan acetate (5% w/v) into a solution of pH 10, is suspended in 5 ml of a solution of glutaraldehyde (5% w/v) dissolved in 50 mM potassium phosphate buffer, pH 7.0. After mixing gently for 60 minutes at 20° C., the activated chitosan particles are recovered by filtration and washed exhaustively with 100 ml of potassium phosphate buffer, or until no glutaraldehyde can be detected in the washings by reaction with 2,4-dinitrophenylhydrazine. The washed chitosan particles are than suspended in 10 ml of potassium phosphate buffer containing pyridoxal phjosphate (1 mM), 2-ketoglutarate (5 mM), and aspartate beta decarboxylase, prepared as in Example 9 (50 mg). After gentle mixing for 90 minutes at 20° C., the chitosan particles containing bound enzyme are collected by filtration, washed with reaction buffer, and finally washed with reaction buffer containing 0.3M NaCl. The immobilized enzyme is stored at 4° C. until ready for use.

Example 12: Immobilization of Aspartate Beta Decarboxylase at Different pH's

Aspartate beta decarboxylase solutions were prepared by disrupting *E. coli* cells containing high levels of aspartate beta decarboxylase as in Example 9. Three one gram portions of cells were separately disrupted and clarified by centrifugation. The immobilization procedure was carried out as described in Example 9 except that the pH of the three enzyme solutions was adjusted to 5.0, 6.0, and 7.0 respectively with hydrochloric acid. The enzyme-containing solutions were recirculated through the support until no further uptake of enzyme was detected by protein and activity assay of the supernatant, and immobilized enzyme was then washed with 0.3M NaCl in potassium phosphate buffer containing pyridoxal phosphate and 2-ketoglutarate The immobilized enzymes were assayed for activity, and the results are shown in the table below.

| Immobilization of Aspartate Beta Decarboxylase | | | |
|---|---|---|---|
| pH of Immobilization | 5.0 | 6.0 | 7.0 |
| Activity Offered (units) | 1000 | 800 | 1100 |
| Activity Bound | 1156 | 898 | 798 |

Example 13:Measurement of the Ratio of Aspartate Beta Decarboxylase to Alanine Racemase Enzymatic Activity A 0.5 gram sample of cells produced as in Example 3 was disrupted using a French Press (Aminco), and the cell debris was removed by centrifugation. The protein-containing supernatant was assayed for both aspartate beta decarboxylase and alanine racemase activities. Aspartate beta decarboxylase was determined by the assay described in Example 1; 1 unit (International Unit) of activity is defined as the conversion of 1 micromole of L-aspartate to L-alanine per minute.

Alanine racemase activity was assayed by the following procedure. A sample of supernatant was incubated in a solution containing Tris citrate buffer (0.1M), L-alanine (0.8M), pyridoxal phosphate (1 mM), 2 ketoglutarate (10 mM), pH 7.5. Aliquots (0.020 ml) were removed from this incubation mixture over time and diluted into a color development reagent consisting of Tris citrate (0.1M), D-amino acid oxidase (1 unit), 4-aminoantipyrine (0.4 mg/ml), and 2,4-dichlorophenol (0.1 mg/ml). The reaction was stopped by the addition of 0.050 ml of 10% SDS. The amount of D-alanine produced was determined by measuring the absorbance at 495 nm and calculating the amount of D-alanine from a standard curve prepared the same day. One unit (International Unit) of alanine racemase activity is defined as the conversion of 1 micromole of L-alanine to D-alanine per minute.

Assays for both aspartate decarboxylase and alanine racemase gave the following result:

| | |
|---|---|
| Aspartate Beta Decarboxylase | 502 units |
| Alanine Racemase | 0.23 units |
| Aspartate Beta Decarboxylase/Alanine Racemase | 2180 |

Example 14:Measurement of the Aspartate Beta Decarboxylase: Alanine Racemase Ratio in an Immobilized Biocatalyst Composition Immobilized biocatalysts were prepared from aspartate beta decarboxylase extracts from recombinant *E. coli* cells by the procedure described in Example 12. The immobilizations were carried out at three different pH's, and the ratio of the aspartate beta decarboxylase: alanine racemase activities bound to the support were measured in each case. The assays were conducted as described earlier, and the results are presented in the table below as the ratio of the enzymatic activities expressed in International Units.

| Activity of Aspartate Beta Decarboxylase Relative To Alanine Racemase in Immobilized Biocatalyst Compositions | | | |
|---|---|---|---|
| | pH | | |
| | 5 | 6 | 7 |
| Asp Beta Decarb (Units) | 1156 | 898 | 798 |
| Ala Rac (Units) | 0.19 | 0.18 | 0.03 |
| ABDC: Ala Rac | 6100 | 5000 | 26000 |

Example 15: Production of L-Alanine

One liter of a 1.5M solution of ammonium aspartate containing pyridoxal phosphate (0.1 mM) and 2-ketoglutarate (2.5 mM), pH 5.5, was recycled using a peristaltic pump through a sample of immobilized aspartate beta decarboxylase prepared as in Example 6 (0.8 gram). The pH of the reservoir was maintained at pH 5.5 by the continuous addition of 6M sulfuric acid mediated by an automatic titrator. The reaction was monitored as a function of time for the production of L-alanine At the end of 68 hours, there was no detectable L-aspartate in the reaction mixture, and assay showed that the L-alanine content had reached 1.5 moles; thus, L-aspartic acid had been converted in 100% yield to L-alanine. Assay of the D-alanine content of the product solution using D-amino acid oxidase showed that D-alanine constituted less than 0.01% of the product. The productivity of the biocatalyst was calculated to be 2.44 grams L-alanine/gram biocatalyst-hour.

Recovery of the L-alanine was accomplished by concentration of the product solution to 40% of its original volume followed by cooling the solution to 0° C. The resulting crystals were collected by filtration, washed with cold 80% aqueous ethanol, and dried at 80° C. The yield was 81 grams (61%). Assay showed D-alanine to constitute 0.0053% of the product.

Example 16: Production of L-Alanine and D-Aspartic Acid

The procedure of Example 15 is repeated except that the substrate for the reaction is D,L-aspartic acid. The product mixture, consisting of an equimolar mixture of L-alanine and D-aspartic acid is recovered by evaporation of the solution. The L-alanine and D-aspartic acid may be separated by techniques known in the art.

What is claimed is:

1. An isolated DNA sequence encoding aspartate beta decarboxylase, said sequence being identical or substantially identical to the coding region of the sequence depicted in FIG. 1 and being free from a nucleotide sequence encoding another enzyme.

2. A vector containing a DNA sequence of claim 1 operably linked to an expression control sequence permitting expression of the DNA sequence and production of aspartate beta decarboxylase in a host microorganism transformed with the vector.

3. A vector of claim 2, wherein the DNA sequence encoding aspartate beta decarboxylase is isolated from *Pseudomonas sp.*

4. A microorganism transformed with a vector of claim 2 or the progeny thereof which is capable of producing aspartate beta decarboxylase.

5. A microorganism of claim 4 or the progeny thereof which produces aspartate beta decarboxylase to the substantial exclusion of alanine racemase.

6. A microorganism of claim 5 or the progeny thereof, wherein the microorganism is a strain of *E. coli*.

7. A method for producing aspartate beta decarboxylase enzyme to the substantial exclusion of alanine racemase which comprises producing a microorganism of claim 4, 5 or 6 and culturing the microorganism under suitable conditions permitting the production of aspartate beta decarboxylase.

8. A method of claim 7, which further comprises lysing or disrupting the cells of the microorganism so cultured and recovering the aspartate beta decarboxylase from cellular debris.

* * * * *